United States Patent

Kim et al.

[11] Patent Number: 5,235,073
[45] Date of Patent: Aug. 10, 1993

[54] POLYETHOXYLATED VITAMIN E

[75] Inventors: Young D. Kim; Byung J. Ha, both of Seoul, Rep. of Korea

[73] Assignee: Pacific Chemical Co., Ltd., Seoul, Rep. of Korea

[21] Appl. No.: 857,652

[22] Filed: Mar. 26, 1992

[30] Foreign Application Priority Data

Mar. 29, 1991 [KR] Rep. of Korea .................. 91-4991
Mar. 2, 1992 [KR] Rep. of Korea .................. 92-3360

[51] Int. Cl.$^5$ .................. C07D 311/72; A61K 31/355
[52] U.S. Cl. .................. 549/408; 252/308
[58] Field of Search .............. 549/408; 514/844, 458; 252/308

[56] References Cited

FOREIGN PATENT DOCUMENTS 0026546 4/1981 European Pat. Off. .
0082569 6/1983 European Pat. Off. .
0090445 10/1983 European Pat. Off. .

Primary Examiner—Nicky Chan
Attorney, Agent, or Firm—Foley & Lardner

[57] ABSTRACT

Polyethoxylated vitamin E having the formula (I):

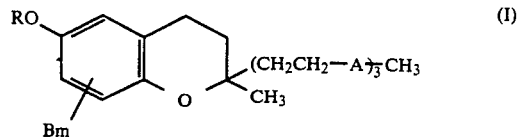

wherein,
R is —$CH_2CH_2)_nH$,
n is an integer from 2 to 100, inclusive,
A is

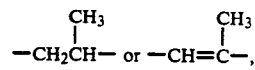

B is —$CH_3$ at the 5-, 7- or 8-position, and
m is 1, 2 or 3.

can be prepared by reacting a vitamin E or an ester thereof with ethylene oxide, using a catalyst under pressure and anhydrous conditions, and shows anti-oxidation and oxidation stability similar to that of vitamin E acetate as well as excellent moisture retention and surfactant activity not shown by vitamin E and vitamin E acetate. Moreover, the compound is highly safe in the living body.

12 Claims, 5 Drawing Sheets

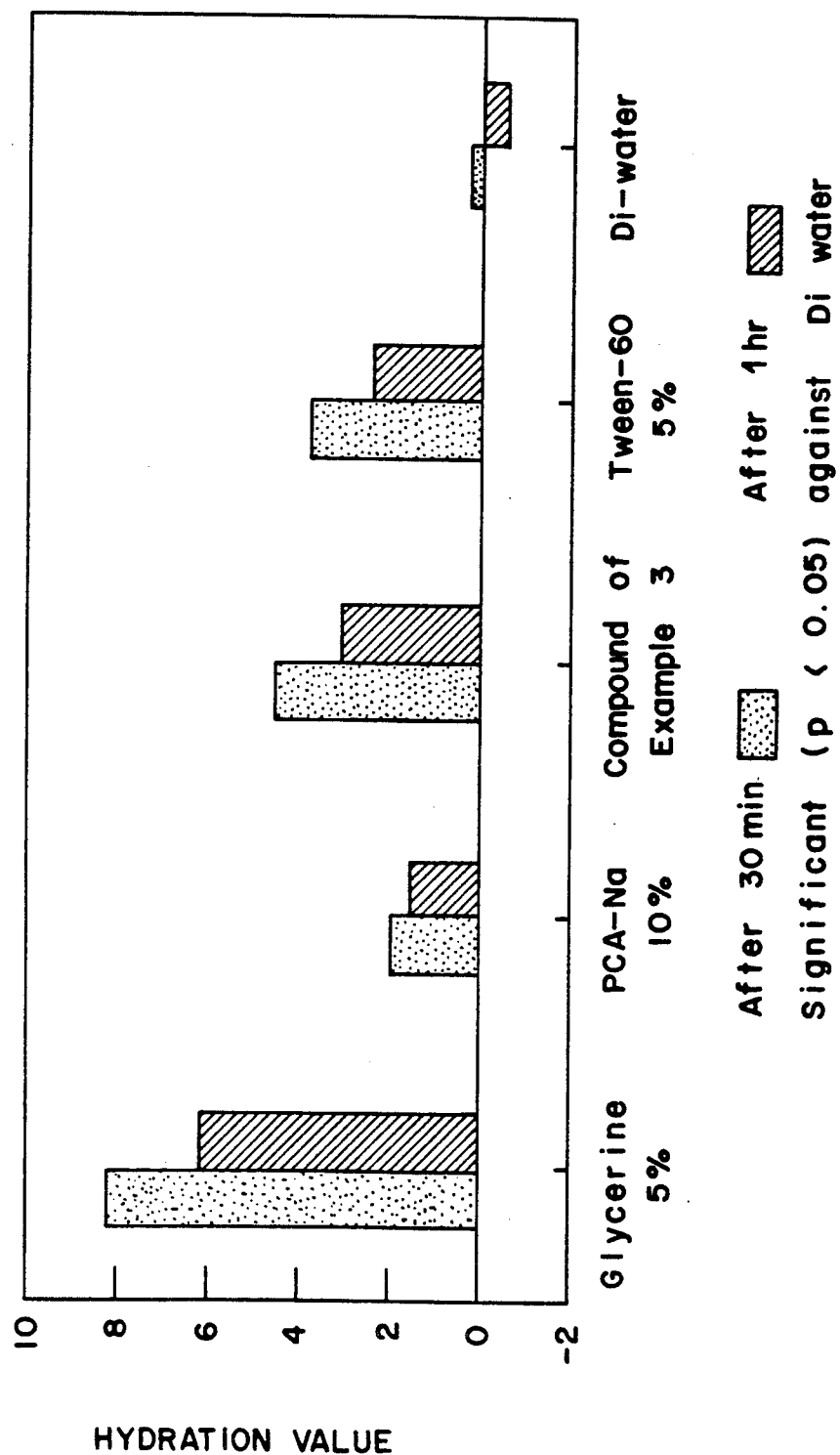

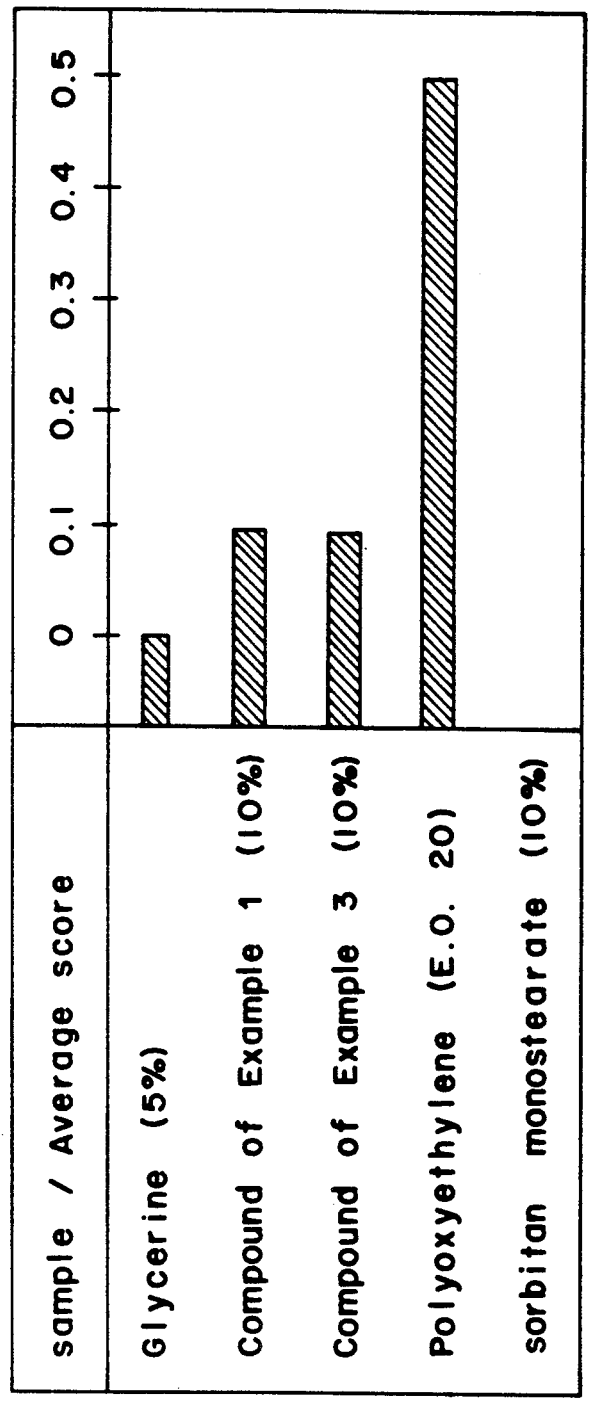

POLYETHOXYLATED VITAMIN E

FIELD OF THE INVENTION

The present invention relates to polyethoxylated vitamin E and to a method for the preparation thereof. More particularly, it relates to polyethoxylated vitamin E having moisture retention, surfactant activity and anti-oxidative effects and to a method for the preparation thereof.

PRIOR ART

Various oil materials such as triglycerides, ester oils or paraffin oil have been widely used as emollients in cosmetics and ointments in order to provide moisture retention effect. Use of such oils in cosmetics and skin ointments requires use of surfactants because these oils have no compatibility with water or water miscible components, which are used as base for the cosmetics and ointments due to their structural characteristics.

Surfactants used in cosmetics, foods and ointment may be classified into emulsifiers, solubilizers, dispersants and foaming agents depending on their function. They also may be classified according to their ionic property into ionic and non-ionic surfactants, and the latter may be further classified into hydrophilic and lipophilic surfactants.

Non-ionic surfactants generally may be prepared by ethoxylating fatty alcohols, alkyl phenols, carboxylic esters, glycerol fatty acid esters, anhydrous sorbitol esters, carboxylic amides, natural fat or oil, or wax with ethylene oxide in the presence of a catalyst by known methods (see Encyclopedia of Chemical Technology, Third Ed., Vol. 22, Surfactant and Detersive System 1978). It is known that the polyethoxylated surfactants having 60–75% of ethylene oxide content show the highest surface activity. However, these non-ionic surfactants show surface activity only, but do not have any physiological activity.

Besides, there are many natural amphoteric biological compounds such as glycolipids, proteins, phospholipids, saponins and bile acids. These compounds are referred to as "bio-surfactant" due to their origin and surface active property. Because of having surface activity, they have an increased water solubility so that they efficiently play their roles in the living body as well as making absorption of other materials easy. Therefore, it is expected for physiological materials for skin care to show improved physiological efficiency due to increased spreadability and absorption if they have surface activity plus their own physiological activities.

Under these considerations, the present inventors have made extensive studies to provide new materials having surface activity as well as their own specific physiological activities. As a result thereof, we found that the above object may be accomplished by subjecting vitamin E having excellent physiological activities to an addition reaction with ethylene oxide to give polyethoxylated vitamin E.

SUMMARY OF THE INVENTION

Thus, an object of the present invention is to provide novel polyethoxylated vitamin E represented by the following formula (I):

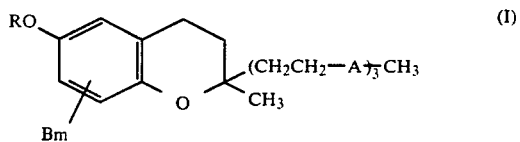

wherein,
R is $-CH_2CH_2O)_nH$,
n is an integer from 2 to 100, inclusive,
A is

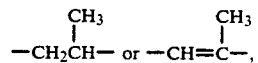

B is $-CH_3$ at the 5-, 7- or 8- position, and
m is 1, 2 or 3.

Another object of the present invention is to provide a process for the preparation of polyethoxylated vitamin E represented by the formula (I) which comprises reacting vitamin E represented by the following formula (II):

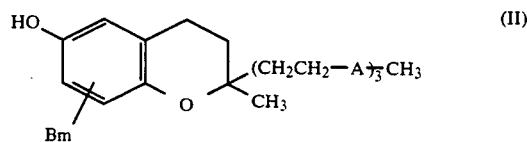

A, B and m have the same meanings as defined above, or an ester thereof with ethylene oxide, in the presence of a catalyst.

Still another object of the present invention is to provide a surfactant comprising the polyethoxylated vitamin E of the formula (I) as an active ingredient.

Another object of the invention is to provide an anti-oxidant comprising the polyethoxylated vitamin E of the formula (I) as an active ingredient.

Another object of the invention is to provide a humectant comprising the polyethoxylated vitamin E of the formula (I) as an active ingredient.

A more complete appreciation of the invention, and many of the additional advantages thereof, will be readily perceived as the said invention becomes better understood by reference to the following detailed description of the invention. Other objects, advantage and features of the present invention will also become apparent to those skilled in the art from the following descriptions.

BRIEF DESCRIPTION OF DRAWINGS

FIG. 6 is a bar graph showing the moisture retention effect of polyethoxylated vitamin E of the present invention; and FIG. 7 is Draize eye irritation scores of polyethoxylated vitamin E of the present invention.

DETAILED DESCRIPTION OF THE INVENTION

Figure 1:
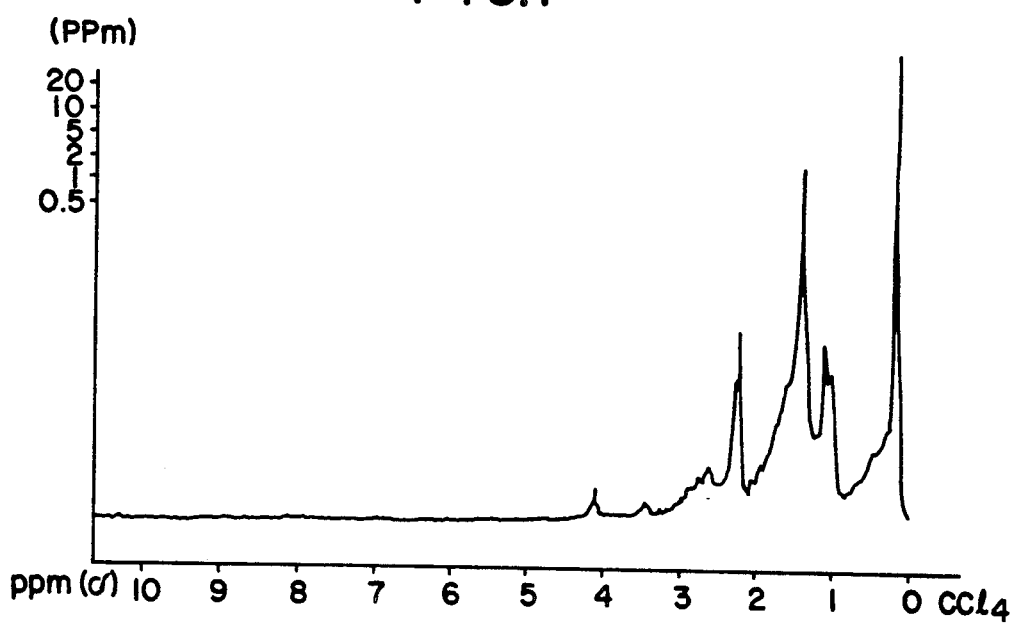
FIG. 1 is a NMR spectrum of synthetic vitamin E (dl-α tocopherol)

Vitamin E is the generic name of a mixture of lipid soluble phenols, tocopherols and tocotrienols possessing general structural features: an aromatic chromanol head and a 16-carbon hydrocarbon tail. The number of methyl substituents in the chromanol nucleus gives rise to $\alpha, \beta, \gamma, \delta$ isomers, whereas the saturation of the hydrocarbon chain differentiates tocopherols with a saturated chain from tocotrienols with an unsaturated chain as forms of vitamin E.

Polyethoxylated vitamin E species of the present invention retain vitamin E's properties such as anti-oxidation and cell protecting activities, since they have a vitamin E skeleton. Further, when they are used in cosmetics, they show a good compatibility with effective water-soluble components of the cosmetic bases and improve the various activities of the components by increasing their substantivity with the skin due to their hydrophilic and surfactive properties which the hydrophobic vitamin E cannot have. Moreover, polyethoxylated vitamin E has moisture retention activity and oxidative stability as well as showing excellent safety in the living body.

Therefore, polyethoxylated vitamin E may be advantageously used in cosmetics, foods or drugs as a humectant, anti-oxidant or surfactant.

The amount of polyethoxylated vitamin E to be added may vary depending on the purpose of addition or kind of materials to which polyethoxylated vitamin E to be added, but generally ranges from about 0.1 to about 50% by weight.

Polyethoxylated vitamin E of the present invention may be prepared by reacting vitamin E with ethylene oxide in the presence of a basic catalyst or a Lewis acid. The reaction advantageously may be carried out under pressure and in the absence of moisture.

For the polyethoxylation of vitamin E, it is very important to control the reaction conditions such as pressure, temperature and amount of catalyst because the initial reaction rate is affected by the steric hindrance of vitamin E. At the beginning, the polyethoxylation of vitamin E proceeds very slowly when compared with that of straight fatty alcohols or alkyl phenols.

Particularly, the fewer the number of mole of ethylene oxide to be added, the more stringent the conditions that are required. Only under such stringent conditions can a narrow distribution of ethylene oxide be accomplished. The average number of ethylene oxide units in the polyethoxylated vitamin E according to the invention can range from 2 to about 100, the lower limit preferably being at least 3.

Vitamin E which is employed in the process of the present invention may be synthetic or natural dl-vitamin E or esters thereof. Vitamin E esters may include the acetate, palmitate, succinate and linolate of vitamin E.

The basic catalysts which may be employed in the process of the present invention can be any strong base, such as hydroxides, alkoxides, hydrides, amides and the like. These include but are not limited to alkali metal hydrides, hydroxides, alkoxides and amides and quaternary ammonium hydroxides, especially NaOH, KOH and NaOCH$_3$. Acid catalysts which may be employed in the process of the invention include any strong acid, preferably a Lewis acid, especially metal halides, which include but are not limited to SbF$_3$ SnCl$_4$ or SbCl$_5$. The catalyst is preferably anhydrous.

The amount of catalyst employed varies depending on the reaction conditions, and preferably ranges from 0.05 to 0.5% based on the weight of vitamin E.

The reaction temperature generally ranges from 120° C. to 180° C., and preferably from 140° to 160° C.

The reaction pressure generally ranges from 1.0 to 8.0 kg/cm$^2$, and preferably from 3.0 to 6.0 kg/cm$^2$.

The present invention being generally described, a more complete understanding can be attained by reference to the examples which are provided herein for purposes of illustration only, and are not intended to limit the invention in any way.

EXAMPLE 1

In a 1 l double stainless steel autoclave were introduced 144 g of synthetic vitamin E (dl-$\alpha$ tocopherol) and 0.2 g of KOH (purity 99.9%) and the moisture inside the reactor was removed by heating to 80° C. under vacuum of about 700 mmHg for 30 min. Then, the relative pressure was adjusted to 0.1 kg/cm$^2$ by using gaseous nitrogen followed by heating to 150° C.

125 g of ethylene oxide was slowly added thereto under the nitrogen atmosphere and the resulting mixture was reacted under stirring for about 5 hours. The pressure was adjusted to 5 kg/cm$^2$ with gaseous nitrogen at the begining of the reaction. As the reaction proceeded, the pressure became low until it kept constant at which the reaction was ended.

After completion of reaction, the reactor was degassed three times with gaseous nitrogen to remove unreacted ethylene oxide and by-produced 1,4-dioxane. The reaction mixture was cooled to about 20° C., at which it remains in liquid state and small amount of acetic acid was added to neutralize the alkaline catalyst. The reaction mixture was washed with benzene to remove unreacted tocopherol and purified by SEPHADEX LH-20, a bead-formed gel prepared by cross-linking dextran with epichlorohydrin, manufactured by SIGMA, U.S.A., column chromatography using chloroformmethanol(1:1) to give 258 g of liquid polyethoxylated vitamin E.

(1) Appearance: liquid at room temperature
(2) Elemental Analysis: as a relative molecular weight of $C_{45}H_{84}C_{10}$

|  | C | H | N |
|---|---|---|---|
| Cal. | 69.02 | 10.55 | 0.00 |
| Exp. | 69.68 | 10.02 | 0.04 |

Figure 2:
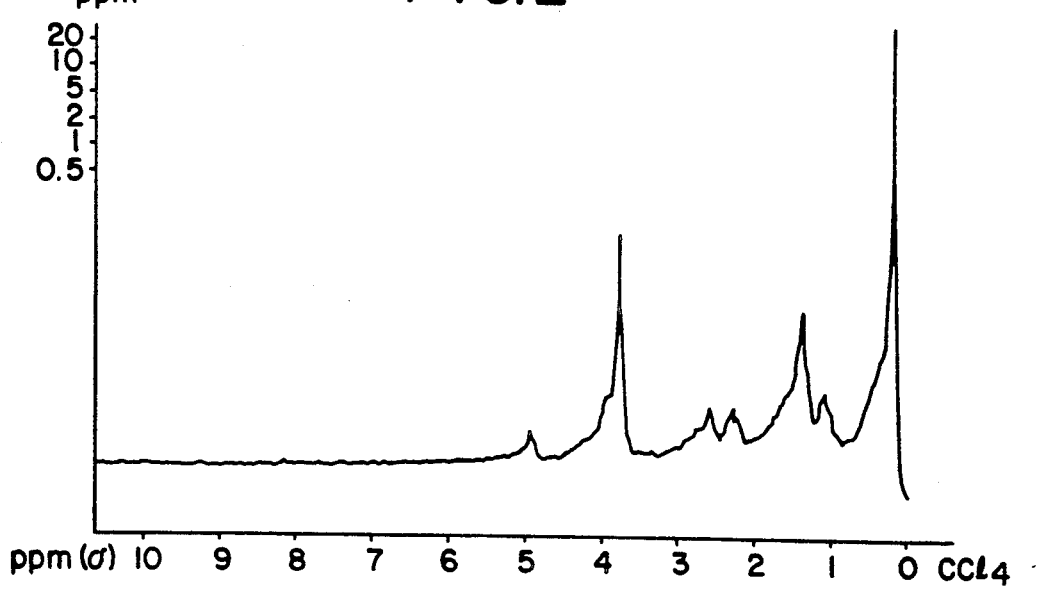
FIG. 2 is a NMR spectrum of polyethoxylated (E.O.=8.07) vitamin E prepared in Example 1 according to the present invention.

(3) Yield: 98.3%
(4) Moles of ethylene oxide added: 8.07 (E.O.=8.07)
(5) NMR spectrum NMR spectra for synthetic vitamin E (dl-$\alpha$ tocopherol) and polyethoxylated vitamin E are shown in FIG. 1 and FIG. 2, respectively. In FIG. 1, which is a NMR spectrum for synthetic vitamin E a peak for —CH$_2$—CH$_2$— or —CH$_3$ appears at 1.17–1.3$\delta$, 3 peaks for —CH$_3$ of the phenyl group at 2.8$\delta$ and peak for the —OH of the trimethylphenol at 4.1$\delta$.

In FIG. 2, which is a NMR spectrum for polyethoxylated vitamin E, the peak at 4.1$\delta$ disappears while a peak for the H of —O—CH₂—CH₂—O— appears at 3.7δ and a peak for the —OH of the end ethylene oxide at 4.8δ.

EXAMPLE 2

In a 1 l double stainless steel autoclave were introduced 144 g of synthetic vitamin E (dl-α tocopherol) and 0.2 g of KOH (purity 99.9%) and the moisture inside the reactor was removed by heating to 85° C. under vacuum of about 700 mmHg for 30 min. Then the relative pressure was adjusted to 0.1 kg/cm² with gaseous nitrogen followed by heating to 140° C.

45 g of ethylene oxide was slowly added thereto under the nitrogen atmosphere and the resulting mixture was reacted under stirring for about 4.5 hours. The pressure was adjusted to 4.8 kg/cm² with gaseous nitrogen at the begining of the reaction. As the reaction proceeded, the pressure became low until it kept constant at which the reaction was ended.

After completion of reaction, the reactor was degassed three times with gaseous nitrogen to remove unreacted ethylene oxide and by-produced 1,4-dioxane. The reaction mixture was cooled to about 12° C., at which it remains in the liquid state and a small amount of citric acid was added to neutralize the alkaline catalyst. The reaction mixture was purified by SEPHADEX LH-20 column chromatography using chloroformmethanol(1:1) to give 181 g of liquid polyethoxylated vitamin E.

(1) Appearance: liquid at room temperature
(2) Elemental Analysis: as a relative molecular weight of $C_{35}H_{61}O_5$

|  | C | H | N |
|---|---|---|---|
| Cal. | 83.83 | 15.97 | 0.00 |
| Exp. | 84.65 | 15.20 | 0.05 |

(3) Yield: 96.1%
(4) Moles of ethylene oxide added: 3.0 at average

EXAMPLE 3

In a 1 l double stainless steel autoclave were introduced 215 g of synthetic vitamin E (dl-α tocopherol) and 0.8 g of KOH (purity 99.9%) and the moisture inside the reactor was removed by heating to 85° C. under vacuum of about 710 mmHg for 40 min. Then, the relative pressure was adjusted to 0.1 kg/cm² with gaseous nitrogen followed by heating to 160° C.

340 g of ethylene oxide was slowly added thereto under the nitrogen atmosphere and the resulting mixture was subjected to addition polymerization under stirring for 6 hours. The pressure was adjusted to 5.2 kg/cm² at the begining of the reaction. As the reaction proceeded, the pressure became low until it kept constant, at which time the reaction was ended.

After completion of reaction, the reactor was degassed four times with gaseous nitrogen to remove unreacted ethylene oxide and by-produced 1,4-dioxane. The reaction mixture was cooled to about 25° C., at which it remains in the liquid state and a small amount of citric acid was added to neutralize the alkaline catalyst. The reaction mixture was purified by SEPHADEX LH-20 column chromatography using chloroformmethanol(1:1) to give 538 g of liquid polyethoxylated vitamin E.

(1) Appearance: semisolid at room temperature
(2) Elemental Analysis: as a relative molecular weight of $C_{59}H_{110}O_{17}$

|  | C | H | N |
|---|---|---|---|
| Cal. | 64.92 | 10.16 | 0.00 |
| Exp. | 65.38 | 10.42 | 0.04 |

Figure 3:
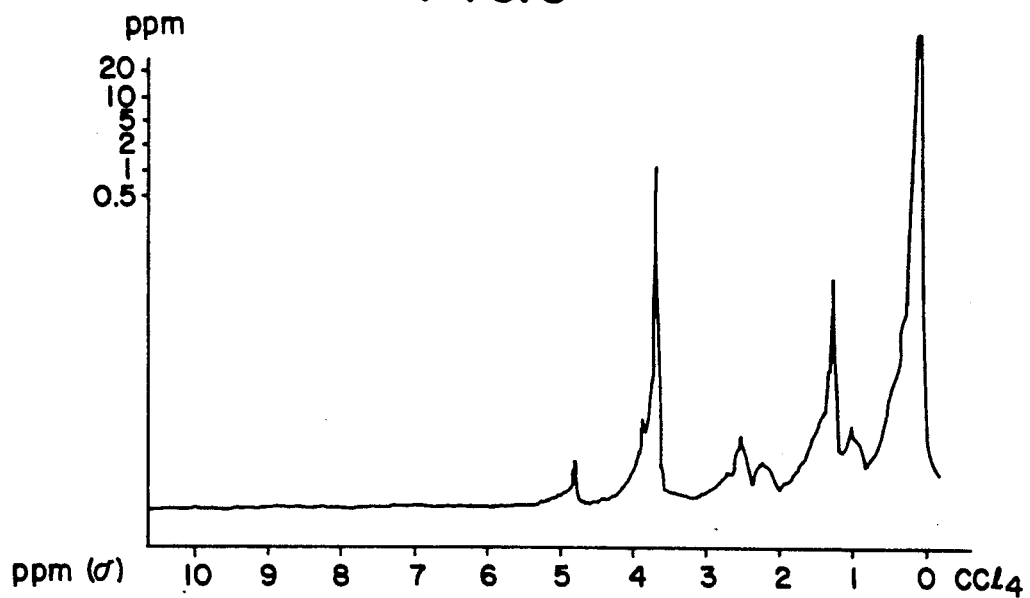
FIG. 3 is a NMR spectrum of polyethoxylated (E.O.=15.02) vitamin E prepared in Example 3 according to the present invention.

(3) Yield: 98.74%
(4) Moles of ethylene oxide added: 15.02
(5) NMR spectrum
NMR spectrum for polyethoxylated vitamin E prepared in Example 3 is shown in FIG. 3. In FIG. 3, the peak for —OH at 4.1δ disappears and a peak for the H of ethylene oxide appears at 3.7δ and is much stronger than that of FIG. 2 since the number of moles of ethylene oxide added in Example 3 is higher than that in Example 1.

EXAMPLE 4

In a 2 l double stainless steel autoclave were introduced 150 g of natural vitamin E and the moisture inside the reactor was removed by heating to 90° C. under vacuum of 0.1 kg/cm² for about 40 min. Then, 2.4 g of NaOH (purity 99.9%) and 470 g of ethylene oxide were successively added under the nitrogen atmosphere. The reaction mixture was reacted under stirring while heating to 160° C. and adjusting the pressure to 5.2 kg/cm² with gaseous nitrogen for 7 hours.

After completion of reaction, the reactor was degassed three times with gaseous nitrogen to remove unreacted ethylene oxide and by-produced 1,4-dioxane. The reaction mixture was cooled to about 45° C., at which it remains in liquid state and a small amount of acetic acid was added to neutralize the alkaline catalyst. Then the reaction mixture was cooled to give 601 g of solid mixture, which was treated with toluene to remove unreacted vitamin E and purified by SEPHADEX LH-20 column chromatography using methanol to give 596 g of solid polyethoxylated vitamin E.

(1) Melting Range: 40°-50° C.
(2) Elemental Analysis: as a relative molecular weight of $C_{89}H_{170}O_{32}$

|  | C | H | N |
|---|---|---|---|
| Cal. | 61.00 | 9.78 | 0.00 |
| Exp. | 60.58 | 10.13 | 0.04 |

Figure 4:
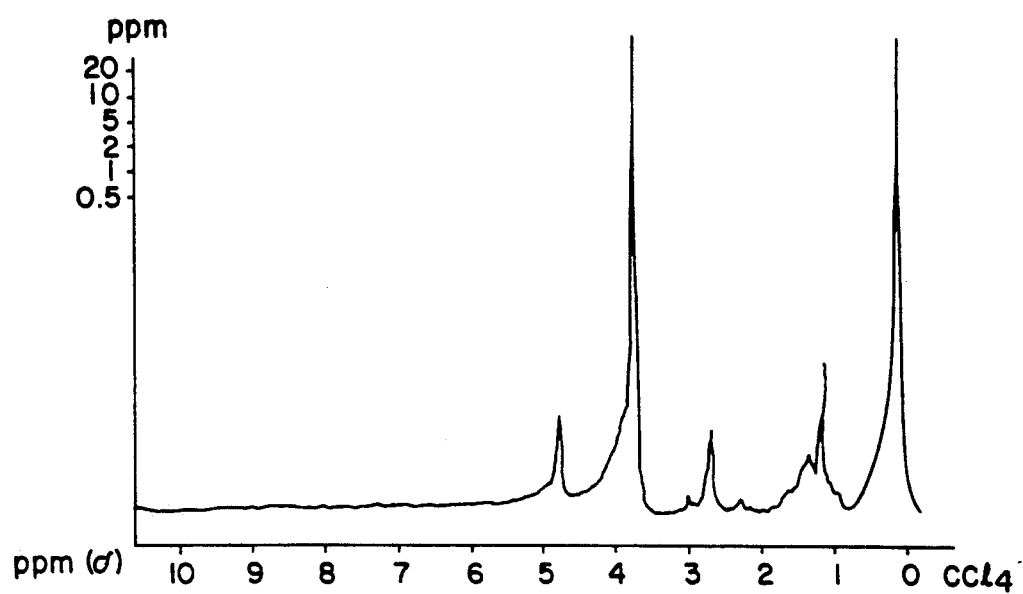
FIG. 4 is a NMR spectrum of polyethoxylated (E.O.=29.93) vitamin E prepared in Example 4 according to the present invention.

(3) Yield: 98.7%
(4) Moles of ethylene oxide added: 29.93
(5) NMR spectrum
NMR spectrum for polyethoxylated vitamin E prepared in Example 4 is shown in FIG. 4. In FIG. 4, the peaks are similar to those in FIG. 3 except that the peak at 3.7δ is much stronger due to an increased moles of ethylene oxide added.

EXAMPLE 5

In a 2 l double stainless steel autoclave were introduced 200 g of synthetic vitamin E (dl-α tocopheryl) acetate and 1.5 g of NaOH (purity 99.9%) and the moisture inside the reactor was removed by heating to 100° C. under vacuum of 0.05 kg/cm² for about 50 min.

1100 g of ethylene oxide was added thereto under the nitrogen atmosphere and the pressure was adjusted to 5.5 kg/cm² with gaseous nitrogen while heating to 150° C. After reaction for 8 hours under stirring, the reactor was degassed twice with gaseous nitrogen to remove unreacted ethylene oxide and by-produced 1,4-dioxane. The reaction mixture was cooled to 60° C., at which it remains in liquid state. The reaction mixture was treated with a small amount of citric acid to neutralize the alkaline catalyst and washed with benzene to remove unreacted vitamin E acetate. Then, the mixture was purified by SEPHADEX LH-20 column chromatography using methanol to give 365 g of solid polyethoxylated vitamin E.

(1) Melting Range: 56°–63° C.
(2) Elemental Analysis: as a relative molecular weight of $C_{129}H_{250}O_{52}$

|  | C | H | N |
|---|---|---|---|
| Cal. | 58.84 | 9.57 | 0.00 |
| Exp. | 58.49 | 9.81 | 0.05 |

(3) Yield: 96.15%
(4) Moles of ethylene oxide added: 51.2
(5) NMR spectrum

Figure 5:
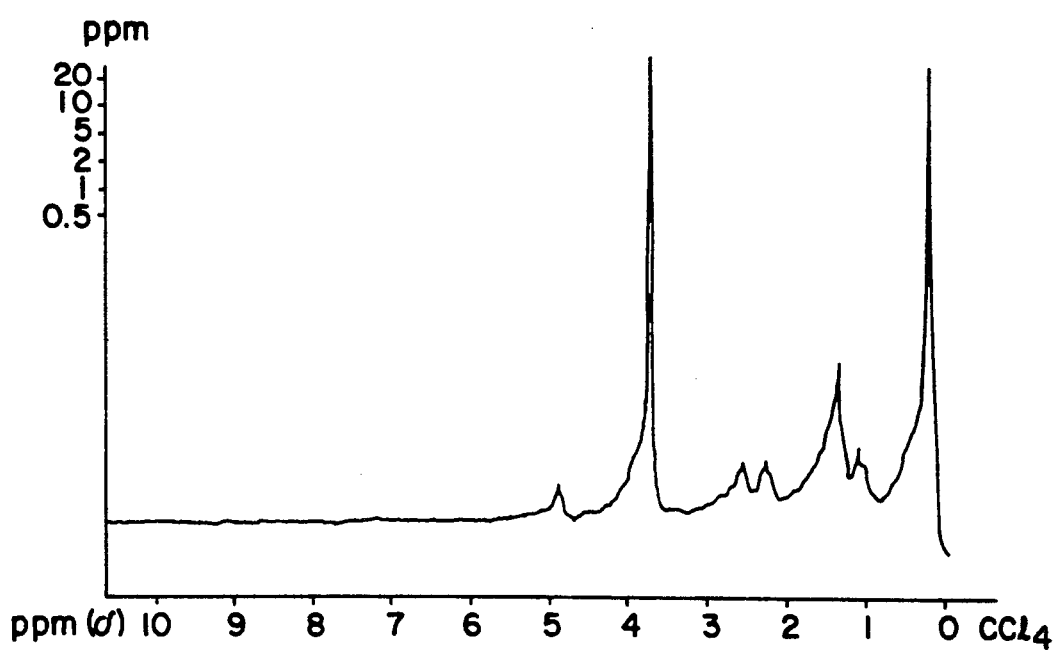
FIG. 5 is a NMR spectrum of polyethoxylated (E.O.=51.20) vitamin E prepared in Example 5 according to the present invention.

NMR spectrum for polyethoxylated vitamin E prepared in Example 5 is shown in FIG. 5. In FIG. 5, the peaks are identical to those in FIG. 3 except that the peak at 3.7δ is much stronger due to the increased number of moles of ethylene oxide added.

EXAMPLE 6

In a 10 l double stainless steel autoclave were introduced 200 g of natural vitamin E, 1.5 g of NaOH (purity 99.9%) and 1.5 g of KOH (99.9%), and the moisture inside the reactor was removed by heating to 110° C. under vacuum of 0.05 kg/cm² for about 60 min.

2100 g of ethylene oxide was added thereto under the nitrogen atmosphere and the pressure was adjusted to 5.6 kg/cm² with gaseous nitrogen while heating to 150° C. After reaction for 10 hours under stirring, the reactor was degassed with gaseous nitrogen to remove unreacted ethylene oxide and by-produced 1,4-dioxane. The reaction mixture was cooled to about 70° C., at which it remains in the liquid state. The reaction mixture was treated with a small amount of citric acid to neutralize the alkaline catalyst and cooled to give 2,135 g of solid polyethoxylated vitamin E.

It is preferred to use excess ethylene oxide to improve the reaction rate, since the purification of the product is hard to carry out when the number of moles of ethylene oxide is high.

(1) Melting Range: 70°–78° C.
(2) Elemental Analysis: as a relative molecular weight of $C_{228}H_{447}O_{102}$

|  | C | H | N |
|---|---|---|---|
| Cal. | 56.82 | 9.28 | 0.00 |
| Exp. | 55.9 | 8.52 | 0.06 |

(3) Yield: 95.70%
(4) Moles of ethylene oxide added: 99.5 at average.

EXAMPLE 7

By following the procedure in Example 1 except that 138 g of β-tocopherol was employed in place of dl-α tocopherol, there was obtained 252 g of liquid polyethoxylated (E.O.=8.07) tocopherol.

EXAMPLE 8

By following the procedure in Example 3 except that 206 g of γ-tocopherol was employed in place of dl-α tocopherol, there was obtained 534 g of semisolid polyethoxylated (E.O.=15.02) tocopherol.

EXAMPLE 9

By following the procedure in Example 4 except that 139 g of δ-tocopherol was employed in place of natural vitamin E, there was obtained 552 g of solid polyethoxylated (E.O.=29.93) tocopherol.

EXAMPLE 10

By following the procedure in Example 5 except that 190 g of dl-β tocopherol acetate was employed in place of vitamin E acetate, there was obtained 347 g of solid polyethoxylated (E.O.=51.2) tocopherol.

EXAMPLE 11

By following the procedure in Example 1 except that 141 g of vitamin E obtained from *Triticum aestivum L.* was employed in place of synthetic vitamin E, there was obtained 253 g of liquid polyethoxylated (E.O.=8.07) tocopherol.

EXAMPLE 12

By following the procedure in Example 3 except that 200 g of vitamin E obtained from *Gossypium indicum LAM* was employed in place of synthetic vitamin E, there was obtained 530 g of semisolid polyethoxylated (E.O.=15.02) tocopherol.

EXAMPLE 13

In a 1 l double stainless steel autoclave were introduced 144 g of synthetic vitamin E (dl-α tocopherol) and 0.14 g of $SbCl_5$(purity 99.9%) and the moisture inside the reactor was removed by heating to 85° C. under vacuum of about 700 mmHg for 30 min. Then the relative pressure was adjusted to 0.1 kg/cm² with gaseous nitrogen followed by heating to 140° C.

45 g of ethylene oxide was slowly added thereto under the nitrogen atmosphere and the resulting mixture was reacted under stirring for about 4.5 hours. The pressure was adjusted to 4.8 kg/cm² with gaseous nitrogen at the begining of the reaction. As the reaction proceeded, the pressure became low until it kept constant at which the reaction was ended.

After completion of reaction, the reactor was degassed three times with gaseous nitrogen to remove unreacted ethylene oxide and by-produced 1,4-dioxane. The reaction mixture was cooled to about 12° C., at which it remains in the liquid state and a small amount of citric acid was added to neutralize the alkaline catalyst. The reaction mixture was purified by SEPHADEX LH-20 column chromatography using chloroformmethanol(1:1) to give 181 g of liquid polyethoxylated vitamin E.

(1) Appearance: liquid at room temperature
(2) Elemental Analysis: as a relative molecular weight of $C_{35}H_{61}O_5$

|  | C | H | N |
|---|---|---|---|
| Cal. | 83.83 | 15.97 | 0.00 |
| Exp. | 83.65 | 15.60 | 0.00 |

(3) Yield: 96.1%

(4) Moles of ethylene oxide added: 3.0 at average

EXPERIMENTAL EXAMPLE 1

Oxidative stability of polyethoxylated vitamin E.

The OH group at the 6-position of vitamin E is susceptible to oxidation by air, light or UV and has a strong reducing ability. Its oxidation is accelerated by the presence of an inorganic salt such as a ferric salt while it shows a considerable stability against heat and alkali. However, when the OH at the 6-position is esterified, the tocopherol is not easily oxidized but it is unstable under alkaline condition and the unstability is increased by heat.

In order to examine the oxidative stability of polyethoxylated vitamin E species according to the present invention, their reducing ability was determined using decoloration of methylene blue by the method described in Japanese Pat. No. Sho 53-2775). 100 mg of each vitamin E, vitamin E acetate or polyethoxylated vitamin E prepared in Example 1 was placed in a test tube and 100 ml of purified water was added thereto. The solution was made weakly alkaline with sodium hydroxide, heated to 60° C. and 10 ml aqueous 0.1% methylene blue solution was added thereto.

The vitamin E solution began to be decolorized after 15 minutes and was totally decolorized after about 1 hour. Thus, tocopherol has a considerable reducing ability.

The vitamin E acetate solution was totally decolorized after about 80 hours while the polyethoxylated vitamin E solution was totally decolorized after about 85 hours. Therefore, polyethoxylated vitamin E has some oxidative stability which is similar to that of vitamin E acetate.

EXPERIMENTAL EXAMPLE 2

Cell protecting action of polyethoxylated vitamin E.

Vitamin E has been reported to have anti-oxidation activity by filtering off the UV light or quenching active oxygens or various free radicals [see. Blacks, HS. Potential Involvement of Free Radical Reactions in Ultraviolet Light-Mediated Cutaneous Damage, Photochem. Photobiol., 45: 213-221 (1987)].

It has been known that free radicals and active oxygen species are generated by an irradiation of UV light and by an enzyme reaction via superoxide ($O^-$) as well as by phagocytosis, immunological stimulation or photosensitization, and are involved in tissue inflamation and oxidative degeneration of cell membrane [See. Krinsky, N. I., Pure and Appl. Chem., 51, 649(1982); Klebanoff, S. J., Ann. Int. Med., 93,480(1980)].

Serveral lines of evidence support the view that singlet oxygen ($^1O_2$) among the reactive oxygen species has the greatest significance in the cells which have endogenous photosensitizable molecules, and frequent opporturnities of being exposed to a variety of xenobiotics. The protein damage in light-exposed skin is the result of singlet oxygen-mediated polymerization and the photocarcinogenesis has been attributed to the action of singlet oxygen. [See Foote, C. S., Photosensitized oxidation and singlet oxygen: Consequences in biological systems, Free Radical in Biology (Pryor, W. A. Ed) Vol. 2, p 85, Academic Press, New York (1976)]

In this invention, singlet oxygen-induced hemolysis using rabbit erythrocytes was evaluated for the polyethoxylated vitamin E as practical protectors for cellular damage caused by singlet oxygen.

In order to examine the cell protecting action of polyethoxylated vitamin E, a photohemolysis test was carried out as follows: [see. S-N Park, D-H Lee, T-Y Lee., J. Soc. Cos. Chemists (Korea), 13, 45(1987)]

Polyethoxylated vitamin E prepared in Example 1, 2, 3 or 4, or vitamin E as a well known anti-oxidant in an amount of 4 mmole was dissolved in 1.0 l of ethanol to obtain test samples.

Blood collected from a rabbit was centrifuged at 8000 rpm for 5 minutes and washed to obtain erythrocytes, which were diluted with physiological saline to give an erythrocyte suspension ($6 \times 10^7$ erythrocytes/3.5 ml).

Six pyrex test tubes of 1.0 cm diameter were prepared and each was charged with 3.5 ml of the suspension. One of the six test tubes was taken as a control group, to which 50 $\mu$l of each sample was added. Six test tubes were preincubated in the dark for 30 minutes.

After completion of preincubation, 0.5 ml of aqueous rosebengal solution (80 $\mu$M) as a photosensitizer was added and the end of the test tube was sealed with a paraffin film. In the center of a $50 \times 20 \times 25$ cm rectangular hexahedron box the inside of which had been painted black was placed a 20 w fluorescent lamp. The test tubes were located at points 5 cm distant from the lamp and were irradiated for 15 minutes.

After completion of irradiation, the transmittances of each test tube kept in the dark at 700 nm were measured at intervals of 15 minutes. The increase in the transmittance of the suspension at this wavelength was proportional to the degree of hemolysis.

Every step of the above experiment was carried out in a constant temperature room at 27° C. The cell protecting activity of the sample against active oxygen species was defined as the time(min) required for hemolyzing 50% of the erythrocytes under the above measurement conditions. The results are shown in Table 1.

TABLE 1

| Cell protecting activity of polyethoxylated vitamin E | |
|---|---|
| sample | cell protecting activity (min) |
| Compound of Example 1 | 185 |
| Compound of Example 2 | 189 |
| Compound of Example 3 | 178 |
| Compound of Example 4 | 160 |
| Tocopherol | 210 |
| Control | 52 |

As shown in the above Table 1, polyethoxylated vatamin E according to the present invention shows a strong activity of as at least three times the control.

EXPERIMENTAL EXAMPLE 3

Anti-oxidation activity of polyethoxylated vitamin E

Anti-oxidation activity was examined for polyethoxylated tocopherols according to the present invention using evening primrose oil. The evening primrose oil may be extracted from seeds of Oenothera, such as *Oenothera odorata Jacquin* or *Oenothera biennis L.* and comprises more than 68% of linoleic acid and more than 7.5% of r-linolenic acid.

0.1% or 1% of polyethoxylated vitamin E prepared in Example 1, or TWEEN-60 (manufactured by ICI, USA, polyethylene glycol (20) sorbitan monostearate), IGEPAL CO-880 (manufactured by GAF, USA, polyethylene glycol(30) nonylphenyl ether) or butylated hydroxytoluene (BHT) as references, was added to the evening primrose oil and was maintained in a constant temperature chamber at 45° C. After two and ten days, a peroxide value (POV) was determined for each sample as follows: Into a 250 ml flask was placed 1.0 g of sample, and 10 ml of chloroform was added to dissolve it. Then 15 ml of glacial acetic acid and 1 ml of saturated potassium iodide solution were added. After a stopper was put on, the flask was vigorously shaken. Free iodine was titrated with a 0.01N solution of sodium thiosulfate, using a starch solution as an indicator, and the point when the solution became colorless was considered as the end point.

$$POV\ (meq/kg) = \frac{(S - B) \times F}{\text{Amount of sample(g)}} \times 100$$

S: Amount of 0.01N sodium thiosulfate solution consumed by sample (ml)
B: Amount of 0.01N sodium thiosulfate solution consumed in blank test tube (ml)
F: Factor of 0.01N sodium thiosulfate solution The results are shown in Table 2.

TABLE 2

| Sample | After 2 days | After 10 days |
| --- | --- | --- |
| Evening primrose oil (at 4° C.) | 12.76 | 12.86 |
| Evening primrose oil (at 45° C.) | 12.70 | 157.77 |
| Evening primrose oil + vitamin E (0.1%) | 20.04 | 60.54 |
| Evening primrose oil + vitamin E acetate (0.1%) | 25.18 | 143.50 |
| Evening primrose oil + Compound of Example 1 (0.1%) | 26.58 | 148.44 |
| Evening primrose oil + Compound of Example 1 (1.0%) | 24.88 | 142.90 |
| Evening primrose oil + Tween 60 (1.0%) | 24.80 | 132.76 |
| Evening primrose oil + Igepal CO 880 (1.0%) | 28.28 | 177.71 |
| Evening primrose oil + BHT (0.1%) | 13.24 | 16.62 |

As can be seen in Table 2, polyethoxylated vitamin E prepared in Example 1 shows an anti-oxidation activity which is similar to that of vitamin E acetate as a reference which is widely used in cosmetics.

EXPERIMENTAL EXAMPLE 4

Action of polyethoxylated vitamin E as a surfactant

In order to examine the surface activity of polyethoxylated vitamin E of the present invention, compounds prepared in Examples, 1, 3, 4 and 5 as well as polyethoxylated (E.O.=24) cholesterol were tested for surface tension, foaming ability and foam stability.

1. Surface tension

The surface tension of 0.1% aqueous solutions of the test compounds were determined with a surface tension balance manufactured by Fisher Scientific using the method of Du Nouy (Du Nouy, "Space Equilibria of Organic and Biological Colloids", Chem. Catalogue, New York, 1926 Science, 69, 251(1929)) at 25° C. The results are shown in Table 3.

TABLE 3

| Sample | Surface tension (dyne/cm) |
| --- | --- |
| Polyethoxylated (E.O. = 24) cholesterol | 37.5 |
| Compound of Example 1 | 56.0 |
| Compound of Example 3 | 49.0 |

TABLE 3-continued

| Sample | Surface tension (dyne/cm) |
| --- | --- |
| Compound of Example 4 | 38.8 |
| Compound of Example 5 | 41.5 |

As shown in Table 3, the polyethoxylated (E.O.=29.93) vitamin E of Example 4 shows the lowest surface tension, 38.8 dyne/cm, which is slightly higher than that of polyethoxylated (E.O.=24) cholesterol as a reference which is widely used in cosmetics.

2. Foaming ability and foam stability

The foaming ability and foam stability were determined by a dynamic foam test.

Into a 2 l scaled cylinder of 10 cm inner diameter was placed 400 cc of 0.1% aqueous solution of the test compounds and the solution was stirred at 3000 rpm, 25° C. with an agimixer. The volume of the resultant foam layer was denoted as the foaming ability, and the ratio of the volume of the foam layer just after stirring to the same three minutes after stirring was denoted as the foam stability. The results are shown in Table 4.

TABLE 4

| Sample | Foaming ability (cc) | Foam stability (%) |
| --- | --- | --- |
| Polyethoxylated (E.O. = 24) cholesterol | 279 | 91.4 |
| Compound of Example 1 | 45 | 66.7 |
| Compound of Example 3 | 220 | 95.5 |
| Compound of Example 4 | 288 | 92.4 |
| Compound of Example 5 | 272 | 93.5 |

As shown in Table 4, the polyethoxylated (E.O.=29.93) vitamin E of Example 4 shows the highest foaming ability, which is slightly higher than that of polyethoxylated (E.O.=24) cholesterol as a reference.

EXPERIMENTAL EXAMPLE 5

Moisture retention effect of polyethoxylated vitamin E

The moisture retention effect of polyethoxylated (E.O.=15.02) vitamin E of Example 3 was compared with those of glycerine, which is most commonly used as a humectant, Tween-60 and pyrrolidone carboxylic acid sodium salt.

Solutions of glycerine (5%), pyrrolidone carboxylic acid-Na (10%), compound of Example 3 (5%) and TWEEN-60 (5%) and distilled water were prepared and applied to the skin of 11 healthy volunteers. 30 min or 1 hour later, the hydrations were determined using Corneometer CM 820PC (Schwarzhaupt, Germany) and the results are shown in FIG. 6.

As shown in FIG. 6, polyethoxylated vitamin E shows a potent moisture retention effect and thus may be effectively used as a humectant in cosmetics.

EXPERIMENTAL EXAMPLE 6

Safety in the living body

1. Eye irritation test

In order to evaluate the safety of polyethoxylated vitamin E of the present invention in a living body, the primary eye irritation test was carried out using a rabbit according to the Draize procedure [J. H. Draize, "Appraisal of the safety of chemicals in food, drug and cosmetics", Association of Food and Drug Officials of the U.S. Topeka 49(1965)].

A test compound selected from polyethoxylated vitamin E of Example 1 or 3, or polyoxyethylene (E.O.=20) sorbitan monostearate was diluted with 10% aqueous glycerine solution to give 10% test samples.

Six healthy albino rabbits weighing 2 to 3 kg were chosen, and 0.1 ml of the test sample was dropped onto one eye of each rabbit, taking the other eye as a control. 24 hours later, the average scores were recorded according to the Draize scoring for ocular lesions. If lesions were present, the time was extended.

The results are shown in FIG. 7. As shown in FIG. 7, the polyethoxylated vitamin E species of the present invention were weaker irritant than polyoxyethylene sorbitan monostearate. Therefore, polyethoxylated vitamin E of the present invention may be safely used in skin-care cosmetics such as eye cream, hair-care cosmetics such as shampoo or rinse and make-up cosmetics such as foundation or lipstick.

2. Patch test

In order to confirm non-toxicity of the polyethoxylated vitamin E on the skin, the human body patch test was carried out by the Finn chamber method involving 20 subjects.

All the subjects were females aged 18–30 years. A test compound selected from polyethoxylated vitamin E of Example 1 or 4, polyoxyethylene (E.O.=20) sorbitan monostearate or polyoxyethylene (E.O.=12) nonyl phenyl ether was dropped onto a brachium of the subject and dermicel tape (Micropore 1530-1 TM, a hypoallergenic tape manufactured by 3M company, USA) was bonded thereto. The skin irritations were evaluated as a response rate (%) according to International Contact Dermatitis Research Group after 24 or 48 hours. The results are shown in Table 5.

TABLE 5

| Test compound | Response rate (%) After 24 hours | After 48 hours |
|---|---|---|
| Compound of Example-1 | 0 | 0 |
| Compound of Example 4 | 0 | 0 |
| Polyoxyethylene (E.O. = 20) sorbitan monostearate | 0.8 | 0 |
| Polyoxyethylene (E.O. = 12) nonyl phenyl ether | 3.0 | 2.8 |

As shown in Table 5, the polyethoxylated vitamin E species of the invention were weaker irritants than polyoxyethylene (E.O.=20) sorbitan monostearate or polyoxyethylene (E.O.=12) nonyl phenyl ether as a control, and thus can be safely used in cosmetics.

As can be seen in the above description, polyethoxylated vitamin E species according to the present invention show anti-oxidation and oxidation stability similar to that of vitamin E acetate as well as showing excellent moisture retention effect and surface activity which are not shown by vitamin E and vitamin E acetate. Moreover, they are highly safe in the living body. Accordingly, polyethoxylated vitamin E of the invention can be advantageously and safely used as a surfactant or humectant in cosmetics, foods and drugs.

While the invention has been described in its preferred forms by way of Examples, it should be understood that the description is for illustrative purpose only, and that changes and modifications may be made by those skilled in the art without departing from the purpose and spirit of the following claims.

What is claimed is:

1. A polyethoxylated vitamin E having formula (I):

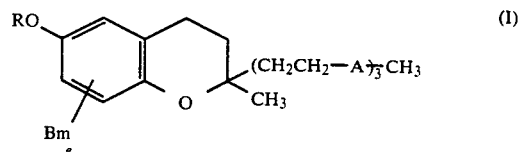

wherein,
R is —CH$_2$CH$_2$O)$_n$H,
n is an integer from 2 to 100, inclusive,
A is

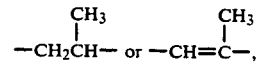

B is —CH$_3$ at the 5-, 7- or 8-position, and
m is 1, 2 or 3.

2. The polyethoxylated vitamin E according to claim 1, which is prepared by a process comprising the step of reacting a vitamin E having by the formula (II):

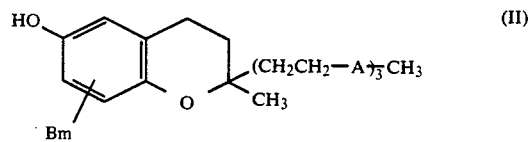

wherein,
A, B and m are as defined for formula I, or an ester thereof, with ethylene oxide, in the presence of a catalyst.

3. The polyethoxylated vitamin E according to claim 2, wherein in said process, said vitamin E is selected from the group consisting of synthetic vitamin E, natural vitamin E and an ester thereof.

4. The polyethoxylated vitamin E according to claim 3, wherein said synthetic vitamin E is selected from the group consisting of dl-α tocopherol, dl-β tocopherol, dl-r tocopherol and dl-δ tocopherol.

5. The polyethoxylated vitamin E according to claim 3, wherein said vitamin E ester is selected from the group consisting of vitamin E acetate, vitamin E succinate, vitamin E palmitate and vitamin E linolate.

6. The polyethoxylated vitamin E according to claim 1, wherein n is an integer from 3 to 100.

7. The polyethoxylated vitamin E according to claim 2, wherein said catalyst is selected from the group consisting of NaOH, KOH and NaOCH$_3$ and used in an amount of 0.05 to 0.5% relative to the weight of vitamin E.

8. The polyethoxylated vitamin E according to claim 2, wherein in said process the reaction temperature is 140° to 160° C.

9. The polyethoxylated vitamin E according to claim 2, wherein in said process the reaction pressure is 3.0 to 6.0 kg/cm$^2$.

10. A surfactant composition which comprises a polyethoxylated vitamin E according to claim 1 as an active ingredient.

11. A cell protecting agent which comprises a polyethoxylated vitamin E according to claim 1 as an active ingredient.

12. A humectant composition which comprises a polyethoxylated vitamin E according to claim 1 as an active ingredient.